United States Patent
D'Spain et al.

(10) Patent No.: US 11,667,619 B2
(45) Date of Patent: Jun. 6, 2023

(54) SYNTHESIS AND PURIFICATION OF CANNABINOL FROM CANNABIDIOL

(71) Applicant: Gaia Botanicals LLC, Louisville, CO (US)

(72) Inventors: Tyler D'Spain, Parker, CO (US); Melanie Hopek, Thornton, CO (US); Coleman Wenzl, Niwot, CO (US)

(73) Assignee: GAIA BOTANICALS LLC, Louisville, CO (US)

( * ) Notice: Subject to any disclaimer, the term of this patent is extended or adjusted under 35 U.S.C. 154(b) by 200 days.

(21) Appl. No.: 16/921,465

(22) Filed: Jul. 6, 2020

(65) Prior Publication Data
US 2022/0002261 A1 Jan. 6, 2022

(51) Int. Cl.
*C07D 311/80* (2006.01)
(52) U.S. Cl.
CPC .................... *C07D 311/80* (2013.01)
(58) Field of Classification Search
None
See application file for complete search history.

(56) References Cited

U.S. PATENT DOCUMENTS

| 8,895,078 B2 | 11/2014 | Mueller |
| 9,867,859 B2 | 1/2018 | Raderman |
| 9,950,976 B1 | 4/2018 | Keller |
| 10,954,208 B2 * | 3/2021 | Webb .................... C07C 37/004 |
| 2006/0167283 A1 | 7/2006 | Flockhart et al. |

FOREIGN PATENT DOCUMENTS

WO 2016004410 A1 1/2016

OTHER PUBLICATIONS

Manoxblog, Cannabis extract purification using orthogonal flash column chromatography, pp. 1-8, Sep. 18, 2019.*

* cited by examiner

*Primary Examiner* — Zinna Northington Davis
(74) *Attorney, Agent, or Firm* — Cowan, Liebowitz & Latman, P.C.; Mark Montague

(57) ABSTRACT

A method to prepare cannabinol (CBN) from derived cannabidiol (CBD) is disclosed. The CBD can be derived from hemp and reacted with a halogen, leading to the cyclization and aromatization of CBD to CBN. The removal of halogen is improved via selective solvent exchange. CBN is isolated from the reaction mixture by use of orthogonal chromatography techniques to provide CBN of high purity.

11 Claims, 3 Drawing Sheets

SYNTHESIS AND PURIFICATION OF CANNABINOL FROM CANNABIDIOL

BACKGROUND OF THE INVENTION

Field of the Invention

The present general inventive concept is directed to a method for preparing cannabinol (CBN) from industrial from industrial hemp derived cannabinoids. The method of the invention can convert cannabidiol (CBD) as well as THC and other naturally occurring or synthetically produced cannabinoids.

Description of the Related Art

The medical benefits of cannabis and cannabinoids have recently become more appreciated in the medical and scientific community. Several compounds present in hemp have been shown to have analgesic or anti-inflammatory benefits. The availability of hemp and cannabinoids free of THC has highlighted the benefits of this class of compounds as they are used by patients without the psychoactive effects of delta-9 tetrahydrocannabinol, or THC. Obtaining cannabinoids free of THC has been recently gaining more attention as the legal standing of hemp in the USA has been altered. Hemp as defined as originating from a plant having less than 0.3% THC has been removed from classification under the Controlled Substances Act. Products with less than 0.3% THC now enjoy a "legal" standing. Conversely, materials with a THC concentration greater than 0.3% on a weight basis are still illegal in some states and legal only with a prescription in other states. Extraction of beneficial compounds from hemp biomass has been the subject of extensive scientific inquiry.

U.S. Pat. No. 9,950,976 to Keller discloses a method for extracting elements and then selectively recovering compounds from solvents. Some methods such as WO2016/004410 disclose the conversion of THC to CBN utilizing the addition of heat in the presence of oxygen over many days, paragraph [0025]. Still other efforts such as U.S. Pat. No. 8,895,078 to Mueller provide a method of increasing THC content by converting CBD to THC.

In nature, cannabinol is only produced from the oxidation of Δ9-THC. With the low Δ9-THC content of industrial hemp, it is not possible to produce appreciable quantities of CBN by oxidation of THC. CBN is of particular interest as an active ingredient as it may be effective as a pain reliever and an anti-inflammatory agent as well as other uses including antibacterial, anticonvulsive, appetite stimulant, eye pressure reliever, as well as other possible uses. Known methods such as U.S. Pat. No. 9,867,859 to Raderman discloses a method of converting THC to CBN by applying heat under vacuum with coconut oil. As high levels of THC are not present in industrial hemp, alternate methods are needed to produce CBN. One available starting material is CBD.

In addition to the synthesis of CBN, efficient and effective purification techniques are needed to produce a high purity product. Available methods of chemical synthesis often produce byproducts, and removal of reagents and intermediates to produce a high purity product is challenging. Effective and efficient purification techniques are needed to obtain suitable products.

What is needed is a method of converting CBD to CBN that does not rely on excessive heat that reduces yield. What is needed is a method of producing CBN and purifying the reaction products to produce a CBN product that is of high purity for human consumption, medical use, or research. The chemical structure of Cannabinol is presented below.

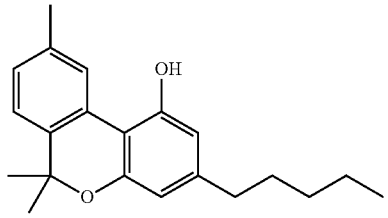 [SMILES: CCCCCc1cc(O)c2c(c1)OC(C)(C)c1ccc(C)cc1-2]

SUMMARY OF THE INVENTION

It is an aspect of the present invention to provide a method for preparing cannabinol from cannabidiol derived from industrial hemp comprising the steps of dissolving CBD in a solvent and reacting CBD with a halogen to cyclize and aromatize the CBD to CBN and create a reaction mixture and purifying the CBN from the reaction mixture by orthogonal chromatography to yield purified CBN.

Cannabidiol serves as a cost-effective starting material that can be converted to cannabinol via a one-pot synthesis. Iodine can be selected as the halogen for its ability to serve as both an oxidizing agent, and an acid, via the formation of hydroiodic acid.

It is a further aspect of the present invention to provide a novel purification method including the steps of chemical quenching, liquid-liquid extraction, solvent exchange, and orthogonal chromatography techniques used to isolate CBN from the reaction mixture. Cannabinol is yielded in a reaction mixture including other tetrahydrocannabinol isomers, residual iodine, and solvent impurities. The application of consecutive purification techniques yields pure CBN, free of iodine and tetrahydrocannabinol impurities.

The present disclosure provides a method of preparing CBN from various isomers of hemp-derived, or synthetic, cannabidiol. Cannabidiol and its double bond and stereoisomers can be converted to tetrahydrocannabinols via acid-catalyzed cyclization. Tetrahydrocannabinols can be reacted with a halogen to promote aromatization to cannabinol. Purified cannabinoids are used as the starting material to limit the number of side-products.

In the preferred embodiment of the invention, cannabinol is prepared by the halogen promoted cyclization and aromatization of cannabidiol. The invention is equally capable of converting tetrahydrocannabinols, such as Δ9-tetrahydrocannabinol (Δ9-THC) to CBN. The application of specific purification techniques allows for the CBN to be purified from the reaction mixture extracting organic material from a biomass of hemp or cannabis and selectively isolating the cannabinoids. It is a further aspect to provide a method for synthesizing cannabinol (CBN) comprising the steps of dissolving CBD in an aromatic solvent; reacting said CBD with a halide under reflux; removing said aromatic solvent to provide a crude product; dissolving said crude product in an aliphatic solvent; quenching said crude product by addition of sodium thiosulfate in solution; drying said crude product with a sequence of brine solution and sodium sulfate; removing said aliphatic solvent to provide crude CBN; performing normal phase chromatography on said crude CBN to provide normal phase CBN; and performing reversed phase chromatography on said normal phase CBN to yield purified CBN.

These together with other aspects and advantages which will be subsequently apparent, reside in the details of the method of the invention as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which.

DESCRIPTION OF THE PREFERRED EMBODIMENTS

Figure 1:
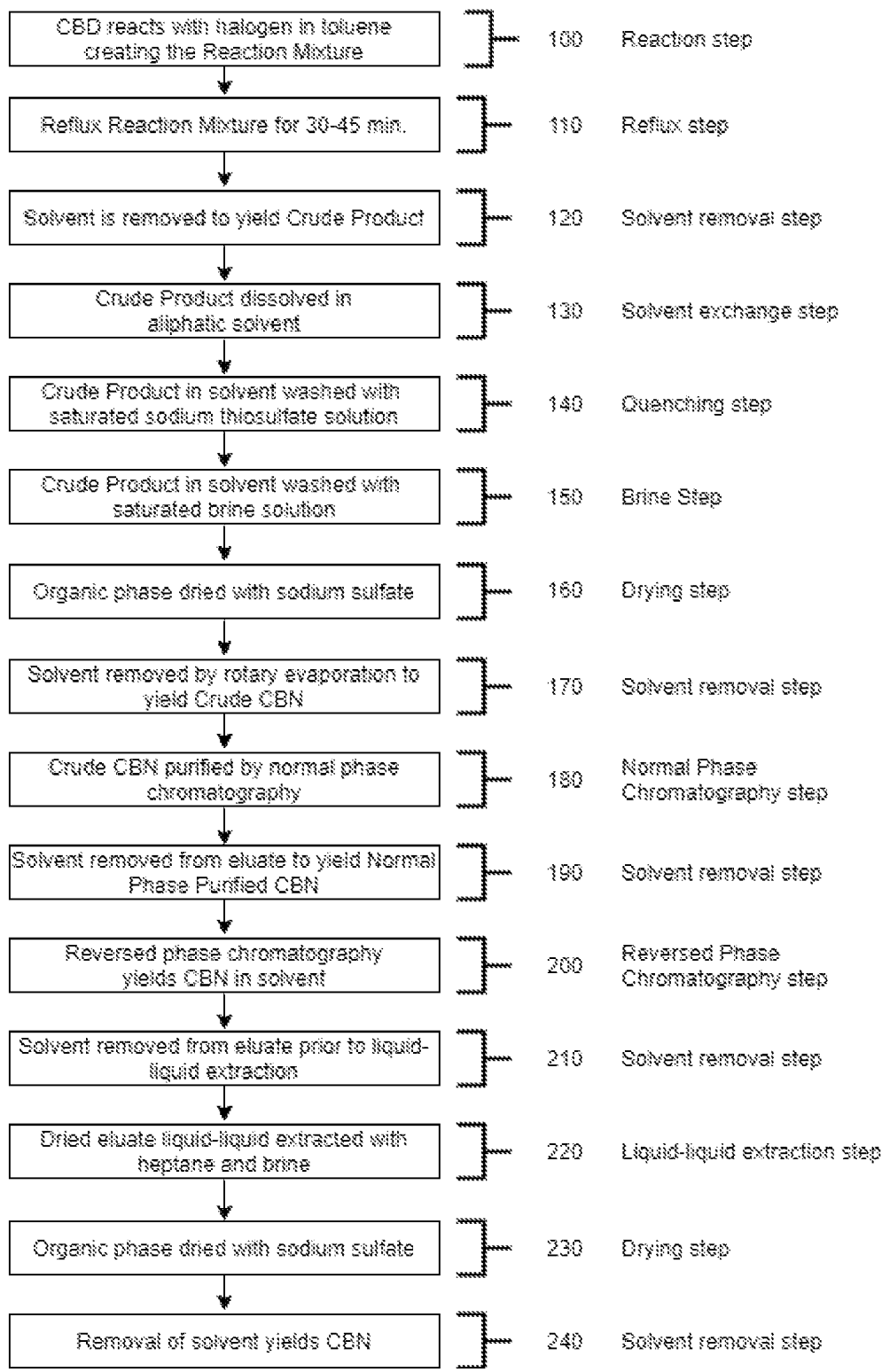
FIG. 1 presents a flow chart of the steps of a method in an embodiment of the invention.

Reference will now be made in detail to the presently preferred embodiments of the invention, examples of which are illustrated in the accompanying drawings, wherein like reference numerals refer to like elements throughout.

The method of the invention may begin with purified cannabidiol (CBD). Alternately, the cannabidiol may be obtained from the extraction of industrial hemp flowers or plant biomass. Extraction of industrial hemp may be performed by ethanol, other alcohols, hydrocarbons such as butane, hexane or heptane, or solvents including supercritical or subcritical $CO_2$, yielding a crude hemp extract. In various embodiments of the invention, the extract is refined by molecular distillation under reduced pressure to obtain a CBD distillate comprising primarily cannabidiol, other cannabinoids including cannabidivarin, tetrahydrocannabinols, cannabichromene, cannabigerol, resins, fats, and oils. The invention is capable of converting tetrahydrocannabinols to cannabinol, but not the remaining components. Tetrahydrocannabinols are not preferably selected as a starting material for the process due to their legal status.

The CBD distillate can be further purified to isolate CBD from the other cannabinoids, resins, fats, and oils. The CBD distillate may be crystallized in a non-polar solvent, such as pentane, hexane, or heptane. The CBD distillate can be heated in a minimal amount of solvent, so that the distillate is only fully solubilized by the solvent while heated. The mixture of solvent and CBD distillate can be cooled slowly to promote the crystallization of CBD. Once fully crystallized, the solids can be filtered and washed with non-polar solvent at −10° C. or colder, yielding CBD of 95% or greater purity.

The conversion of CBD in a pure form or in combination with other related compounds or impurities can be accomplished in a synthesis comprising the following steps. FIG. 1 presents a flow chart of the steps of a method in an embodiment of the invention. In reaction step 100, CBD can be reacted with a halogen in a solvent, e.g. toluene, at an elevated temperature. The mechanism most likely consists of a series of addition/elimination reactions of iodine across available double bonds. Upon the elimination, a hydrogen halide is formed through the loss of a hydrogen from the cannabinoid. The hydrogen halide can catalyze the cyclization of CBD to a hydrocannabinol. The addition/elimination of halogen across the double bonds continues until the hydrocannabinols are fully oxidized to cannabinol. The reaction temperature and duration may be modified to vary the yield and side products of the reaction. In a preferred embodiment, the reaction mixture of reaction step 100 is subject to reflux step 110 at approximately 110° C. for 10 to 60 minutes. Preferably, reflux step 100 is conducted between 30 and 45 minutes.

The halogen utilized in the conversion may consist of bromine, chlorine, or iodine, in pure form. In a preferred embodiment, iodine is utilized as the halogen. Bromine and chlorine are alternatives, but the volatility of these halogens increase the complexity of the required apparatus. The halogen may be provided with a purity of 99.5% (w/w) or greater to reduce the complexity of the reaction mixture and simplify the purification. In various embodiments, the halogen may be provided at about 1 to 3 moles of molecular halogen for every mole of CBD. If too little halogen is used, the reaction yield will be reduced. If too much halogen is used, the rate of the reaction will increase, but at increased cost and complexity of reaction by-products that may be degraded by excess halogen amounts.

In an example, where the reaction was allowed to proceed for 60 minutes, the yield of CBN was reduced and an unidentified, difficult to separate tetrahydrocannabinol isomer observed. After the reaction has progressed for the desired duration, the solvent can be removed in solvent removal step 120 for example by rotary evaporation under reduced pressure and elevated temperature yielding the crude product. Solvent removal step 120 also provides the benefit of removing volatile colored reaction products, turning the recovered solvent pink.

Solvent exchange step 130 comprises dissolving the crude product in a non-polar, aliphatic solvent, which reduces the solubility of the halogen. The non-polar solvent may be either pentane, hexane, cyclohexane, heptane, or any mixture thereof. The exchange of solvent from toluene to an aliphatic hydrocarbon is critical to ensure the removal of iodine in the following steps.

In quenching step 140, the solution of crude product is washed with a saturated solution of sodium thiosulfate, such that a minimum of 2 moles of thiosulfate are used per mole of halogen. The sodium thiosulfate reacts with iodine to form sodium iodide, which is water-soluble and can be removed by liquid-liquid extraction. Quenching step 140 also comprises liquid-liquid extraction where the aqueous phase is partitioned and removed, providing removal of most of the sodium thiosulfate and sodium iodide.

In brine step 150 the organic phase is washed with brine, a saturated solution of sodium chloride in water, which is then removed by liquid-liquid extraction. The brine solution aids in the removal of water from the organic phase. In the liquid-liquid extraction, the aqueous phase is partitioned and removed resulting in the removal of the brine, additional water from the organic phase, and any remaining sodium iodide or sodium thiosulfate.

In drying step 160 the organic phase is dried with the addition of sodium sulfate or magnesium sulfate, and the solution is filtered to remove the sodium or magnesium sulfate.

In solvent removal step 170, the aliphatic solvent is removed by rotary evaporation yielding crude CBN, with a CBN concentration ranging from 15% (w/w) to 30% (w/w). A temperature within 20° C. of the solvent's boiling point is used to ensure the full removal of the non-polar solvent.

At this point in the method, the reaction is complete and a significant portion of the CBD starting material has been converted to CBN. However, reaction side products are present and are preferably removed to provide pure CBN. The crude CBN may be purified using an orthogonal succession of normal phase chromatography followed by reversed phase flash chromatography. It has been discovered that a sequence of chromatography utilizing a polar stationary phase followed by chromatography utilizing a non-polar stationary phase can provide a multistep purification process with excellent results. In particular, normal phase chromatography may be performed in normal phase chromatography step 180, for example, by chromatography using silica-gel as the stationary phase and a solvent selected from the group of pentane/hexane/heptane or petroleum ether in combination with ethyl acetate as the mobile phase. Chromatography using silica-gel media provides removal of highly polar and colored byproducts that are trapped by the silica gel. These are likely halogenated intermediates, and other reaction byproducts. The eluate is collected as one fraction, which is dried in solvent removal step 190 comprising rotary evaporation under vacuum with a temperature between 75-85° C.

Reversed phase chromatography step 200 can comprise reversed phase flash chromatography performed using C18 coated silica-gel as the stationary phase with ethanol or methanol mixed with water as the mobile phase. Mobile phase gradient programming is used to control the eluent strength throughout the run. Reversed phase chromatography effectively separates tetrahydrocannabinol impurities from the normal phase purified CBN, yielding CBN in solvent. The eluate is collected in 25 mL fractions, which are tested by HPLC-DAD to confirm purity. A small sample of the fraction is diluted 200-fold with methanol, filtered using a PTFE syringe filter, and analyzed. The peak purity is determined at 228 nm. All fractions with peak purity of CBN greater than 95% are combined. To improve phase separation, the methanol may be removed by rotary evaporation under vacuum in solvent removal step 210 until the solution turns milky white. The non-polar solvent, pentane/hexane/heptane or petroleum ether is added to extract CBN. Once the two solvents are shaken vigorously, the aqueous and organic phases are allowed to separate. The aqueous phase is drained to waste, and the organic phase is collected. Another liquid-liquid extraction step 220 is performed to transfer the CBN from the water and methanol solution, to a non-polar organic solvent. In drying step 230 the organic phase is dried with magnesium or sodium sulfate, filtered to remove the magnesium or sodium sulfate, then the solvent is removed. The solvent may be removed by rotary evaporation in solvent removal step 240 to yield CBN. Rotary evaporation is performed below 20 mTorr and 75-85° C. to ensure full removal of solvents. In various embodiments, CBN is obtained at purity of 95% to greater than 99%.

The following examples present various aspects of the invention, illustrating advantages obtained by the present invention compared to alternative methods. As used herein, the term "about" refers to a +/− variation of 10% from any given value. It may be understood that variation is always included in a given value unless provided herein, whether or not it is specifically referred to. All chemicals, reagents, and solvents used in the present examples were purchased from Sigma-Aldrich and used as-is unless specified otherwise.

Example 1: Preparation of CBN

Figure 2:
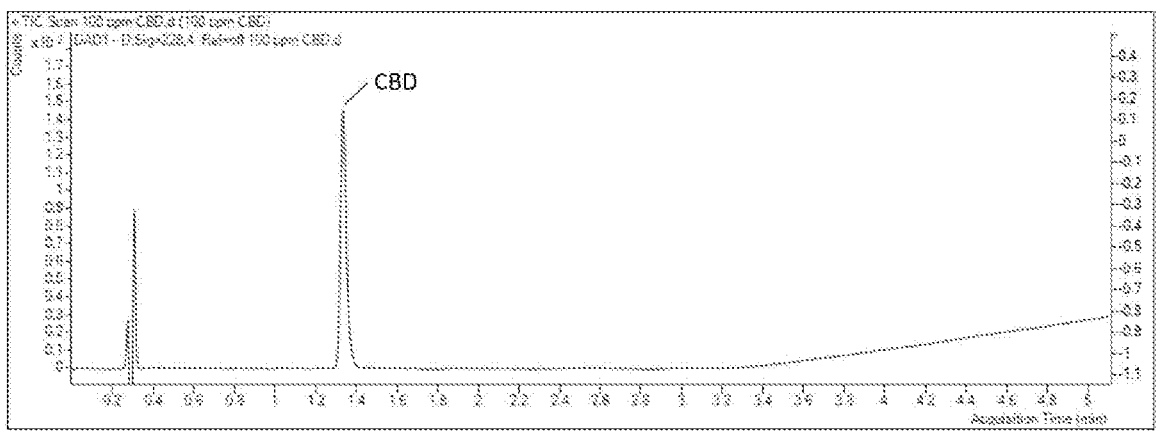
FIG. 2 shows an HPLC chromatograms of cannabidiol starting material.
Figure 3:
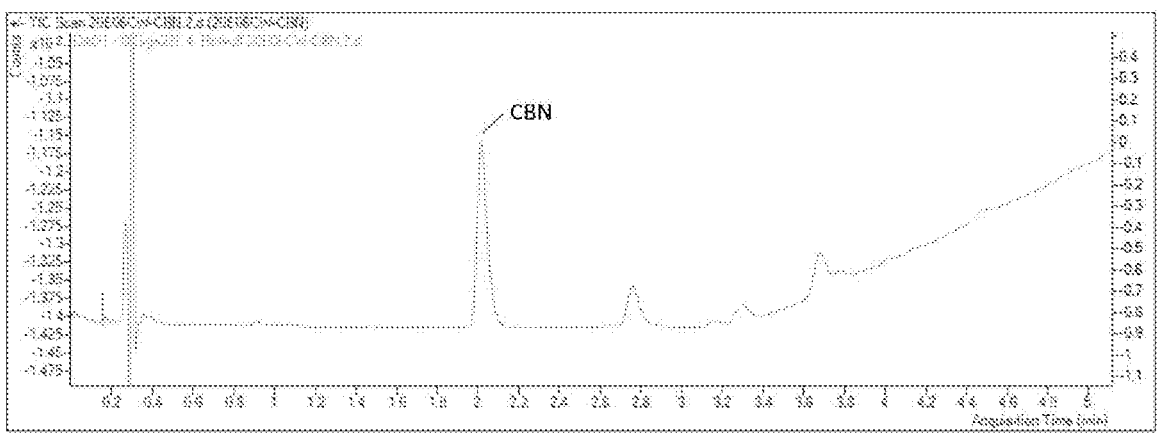
FIG. 3 shows an HPLC chromatogram of crude reaction mixture after aromatization and halogen quenching.

Reaction step 100 comprises a starting compound of 16 g of Cannabidiol (CBD) with 99%+ purity. FIG. 2 presents an HPLC chromatogram of CBD starting material. The peak is labeled CBD. In this example the CBD staring material was obtained from CBD CliniLabs of Denver, Colo. and dissolved in 400 ml of toluene followed by addition of 25.9 g of iodine. Reflux step 110 was conducted where the reaction mixture was refluxed with stirring at about 110° C. for 45 minutes. The reaction mixture was then allowed to cool to room temperature, about 23° C. The reaction mixture was then filtered and dried by rotary evaporation at about 45° C. and 5 to 50 torr in solvent removal step 120 yielding crude product. In solvent exchange step 130, the crude product was dissolved in heptane (400 mL) from TDA Chemical. In quenching step 140, crude product was washed with a saturated solution of sodium thiosulfate (2 L proportioned over 5 consecutive washes). Brine step 150 comprised a brine wash (400 mL) of saturated sodium chloride in water. In drying step 160, the solution of crude product was dried with sodium sulfate (10 g) and filtered to remove solids. Solvent removal step 170 was conducted comprising rotary evaporation, yielding 10-15 g of crude CBN (15-30% w/w). The crude CBN was analyzed for purity; FIG. 3 presents an HPLC chromatogram of crude CBN showing CBN at 2.05 minutes, along with various tetrahydrocannabinol isomers and other unidentified impurities.

Example 2: Purification of CBN

Figure 4:
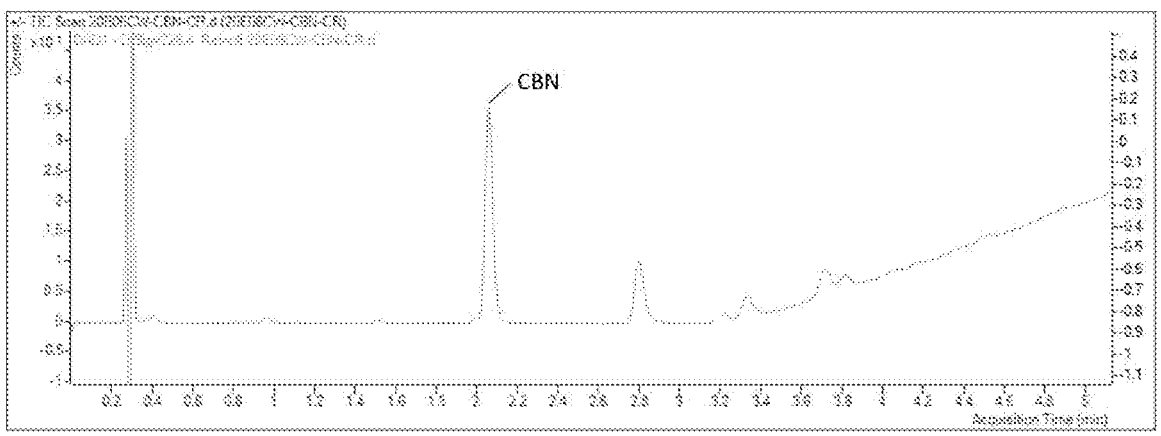
FIG. 4 shows an HPLC chromatogram following normal phase chromatography purification.

Normal phase chromatography step 180 was conducted with the crude CBN (15 g) dissolved in heptane (15 mL) and purified by vacuum normal phase chromatography by loading the mixture onto silica gel (100 g) and eluted with 9:1 heptane/ethyl acetate (1000 mL). The entire eluate, consisting of CBN, the tetrahydrocannabinols and other similar impurities is collected. The silica removes only highly polar contaminants. In solvent removal step 190, the eluent was dried by rotary evaporation yielding normal phase purified CBN (12.5 g, 25-30% w/w). Analytical methods were utilized to determine the purity of the normal phase purified CBN. FIG. 4 presents an HPLC chromatogram of the normal phase purified CBN following normal phase chromatography, displaying the CBN peak at 2.05 minutes along with tetrahydrocannabinols and other cannabinol-like impurities.

Reversed phase chromatography step 200 was conducted with the normal phase purified CBN (12.5 g) dissolved in dimethylformamide (DMF) (12.5 mL) and purified by reversed phase flash chromatography on an 1850 g C18 coated silica gel flash cartridge. Utilizing gradient programming, the mixture was separated by gradient elution of methanol-water from 75% to 95% methanol controlled by gradient programming over 65 minutes with a flow rate of 500 mL/min. The eluate was collected in 25 mL fractions. The CBN containing fractions were analyzed by HPLC-DAD to confirm purity. In solvent removal step 210, the CBN containing fractions were combined, and the solvent was removed by rotary evaporation until the mixture turned milky white. In liquid-liquid extraction step 220, heptane (500 mL) and brine (250 mL) were added and the solution was mixed vigorously, then allowed to separate in a glass separatory funnel. The aqueous layer was drained, then in drying step 230, sodium sulfate was added (10 g) followed by mixing, then the solution was filtered to remove the sodium sulfate. In solvent removal step 240, the organic phase was dried by rotary evaporation, yielding CBN (2.5 g, 95-100% w/w).

Figure 5:
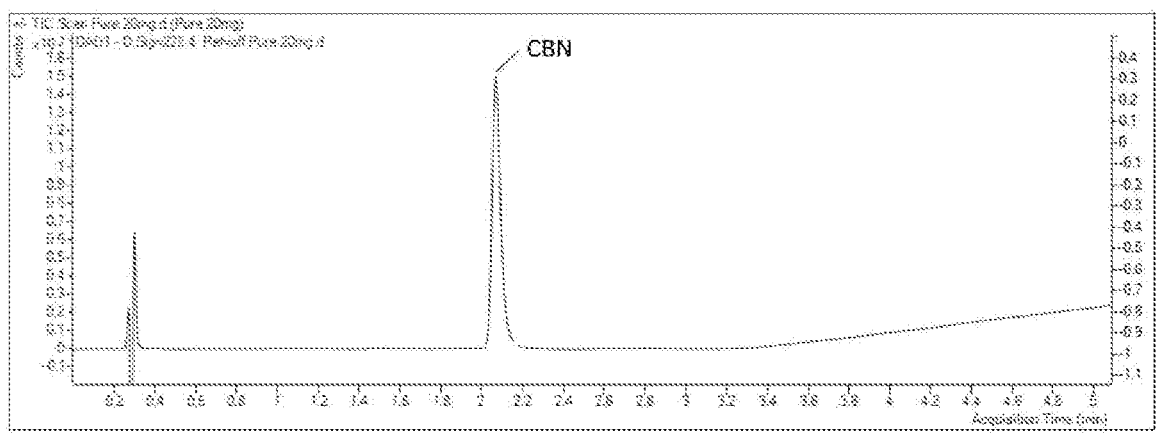
FIG. 5 shows an HPLC chromatogram following reversed phase flash chromatography purification.

FIG. 5 presents an HPLC chromatogram following purification by reversed phase flash chromatography step 200, and the steps detailed above through solvent removal step 240. The only peak detected was CBN and is labeled in the figure. Purity was determined by high performance liquid chromatography with a diode array detector (HPLC-DAD). Compound identities were confirmed by their retention times and mass-to-charge ratios. Mass-to charge ratios were determined by liquid chromatography-positive electrospray ionization mass spectrometry (HPLC-ESI-MS). The separations were performed on an end-capped C18 column by gradient elution with water (10 mmol ammonium formate, pH 3.6) and acetonitrile containing 0.1% formic acid. Purity was determined at 228 nm by peak area %. The most prevalent impurities from the synthesis were determined to be tetrahydrocannabinol isomers by their mass-to-charge ratios. The final CBN obtained from the invention is free of THC and suitable for medical use and complies with laws prohibiting the presence of THC. Other analytical methods known in the art, or novel, can be utilized to determine product purity.

Any description of a component or embodiment herein also includes hardware, software, and configurations which already exist in the prior art and may be necessary to the operation of such component(s) or embodiment(s). Further, the operations described herein can be performed in any sensible order. Any operations not required for proper operation can be optional.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method for producing and purifying cannabinol (CBN) from cannabidiol (CBD) comprising the steps of:
    dissolving CBD in a solvent;
    reacting CBD with a halogen to cyclize and aromatize the CBD to CBN and create a reaction mixture;
    decreasing the solubility of said iodine by solvent exchanging said reaction mixture with an alkane to decrease solubility of the halogen; and
    purifying of CBN from said reaction mixture by normal phase chromatography and reversed phase chromatography to yield purified CBN.

2. The method of claim 1, wherein said solvent is toluene.

3. The method of claim 2, wherein said halogen is iodine.

4. The method of claim 1, wherein said alkane comprises heptane.

5. The method of claim 1, wherein said normal phase chromatography is performed on silica gel stationary phase with heptane-ethyl acetate mobile phase.

6. The method of claim 5, wherein said reversed phase chromatography is performed on C18 silica gel with methanol-water mobile phase.

7. The method of claim 6 wherein said reversed phase chromatography is performed after said normal phase chromatography.

8. The method of claim 6, wherein said reversed phase chromatography comprises a diluent for column loading consisting of dimethylformamide.

9. The method of claim 8 wherein said CBD is derived from hemp.

10. The method of claim 1, wherein the purified CBN has a purity of at least 95%.

11. The method of claim 1, wherein the alkane is selected from the group consisting of pentane, hexane, cyclohexane, heptane, or any mixture thereof.

* * * * *